United States Patent [19]

Dutcher

[11] 4,381,013
[45] Apr. 26, 1983

[54] "J" STYLET WIRE

[75] Inventor: Robert G. Dutcher, Columbia Heights, Minn.

[73] Assignee: Medtronic, Inc., Minneapolis, Minn.

[21] Appl. No.: 244,933

[22] Filed: Mar. 19, 1981

[51] Int. Cl.³ .............................................. A61N 1/36
[52] U.S. Cl. .............................. 128/785; 128/419 P; 128/786
[58] Field of Search ............ 128/419 P, 348, 784–786, 128/DIG. 9, 642, 656–658, 772, 349 R

[56] References Cited

U.S. PATENT DOCUMENTS

| | | | |
|---|---|---|---|
| 3,547,103 | 12/1970 | Cook | 128/772 |
| 3,788,329 | 1/1974 | Friedman | 128/419 P X |
| 3,844,292 | 10/1974 | Bolduc | 128/419 P X |
| 3,890,977 | 6/1975 | Wilson | 128/418 |
| 3,974,834 | 8/1976 | Kane | 128/419 P X |
| 3,995,623 | 12/1976 | Blake et al. | 128/419 P X |
| 4,020,829 | 5/1977 | Wilson et al. | 128/348 X |
| 4,046,151 | 9/1977 | Rose | 128/419 P X |
| 4,106,512 | 8/1978 | Bisping | 128/419 P X |
| 4,136,701 | 1/1979 | Barton et al. | 128/419 P X |
| 4,136,703 | 1/1979 | Wittkampf | 128/419 P |
| 4,146,036 | 3/1979 | Dutcher et al. | 128/785 |
| 4,180,080 | 12/1979 | Murphy | 128/642 |
| 4,209,019 | 6/1980 | Dutcher et al. | 128/419 P |
| 4,215,703 | 8/1980 | Wilson | 128/772 |
| 4,217,913 | 8/1980 | Dutcher | 128/419 P X |

*Primary Examiner*—Kyle L. Howell
*Assistant Examiner*—Angela D. Sykes
*Attorney, Agent, or Firm*—Reed A. Duthler; John L. Rooney; Joseph F. Breimayer

[57] ABSTRACT

A body implantable lead having a two-piece stylet. An inner solid portion of the stylet enables a shape to be imparted to the stylet to allow proper maneuvering of the lead during implant. A second portion of the stylet is slideably located coaxially about the first portion. The second portion of the stylet permits the imposition of a torque at the distal end of the implantable lead by the turning of a knob fixedly attached to the proximal end of the second portion of the stylet. The second portion of the stylet is a helically wound coil. The two-piece stylet is inserted into the proximal end of the body implantable lead. The distal end of the body implantable lead is located in the position desired through the use of the solid inner first portion of the stylet in which a bend or other desired shape has been introduced. The body implantable lead is permanently attached to the muscle tissue by a fixation device activated through the torque supplied by the second portion of the stylet. The two portions of the stylet may be fabricated from a variety of materials.

19 Claims, 7 Drawing Figures

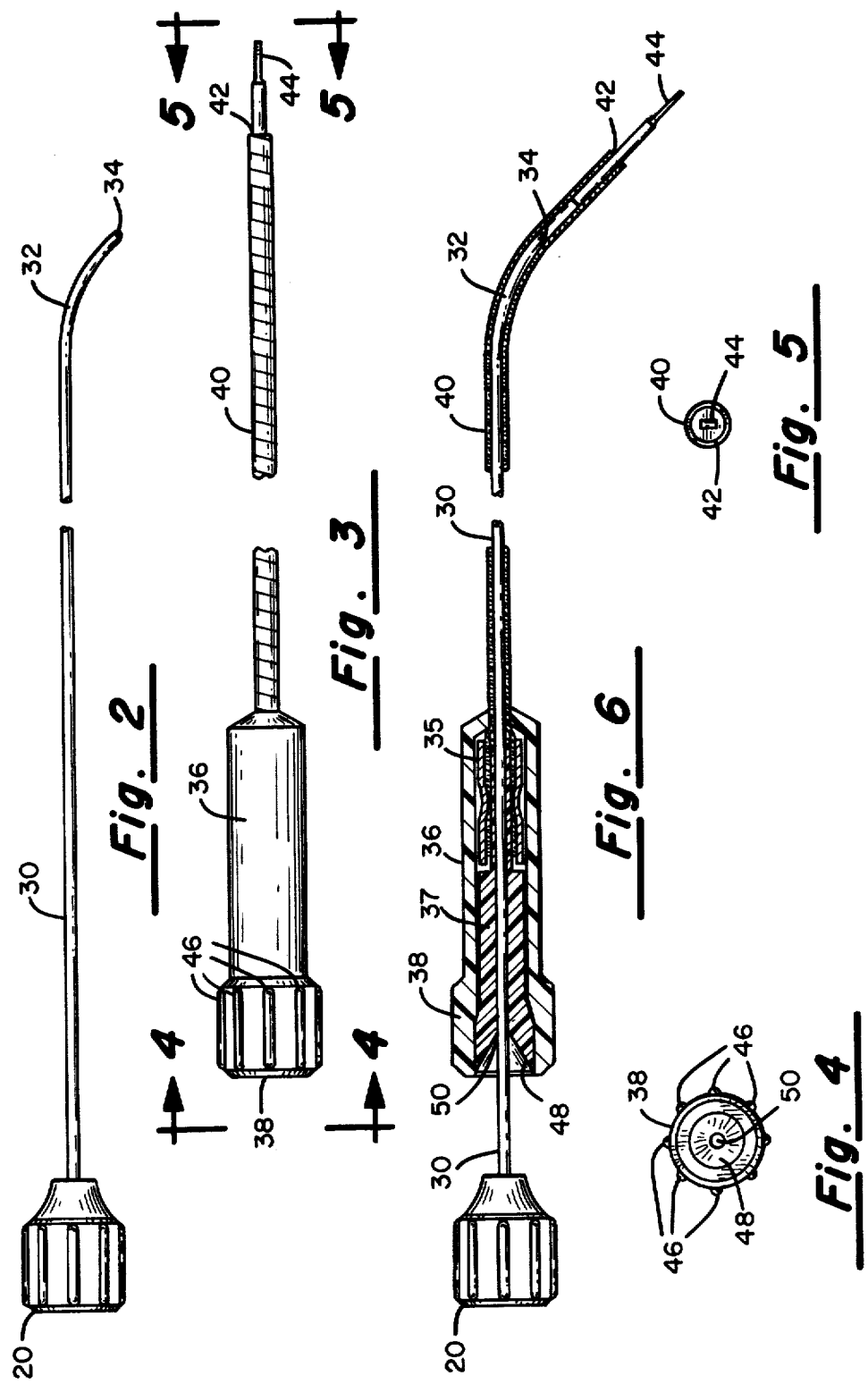

"J" STYLET WIRE

CROSS-REFERENCE TO CO-PENDING APPLICATION

Attention is drawn to the following commonly assigned co-pending patent application:

Flexible Tip Stiffening Stylet for Use With Body Implantable Lead by Dutcher et al, Ser. No. 1,203, filed Jan. 5, 1979 now abandoned in favor of continuing application Ser. No. 176,410, filed on Aug. 8, 1980.

BACKGROUND OF THE INVENTION

1. Field of the Invention

The present invention relates generally to electrical devices for medical application, and more specifically relates to chronically implantable electrodes.

2. Description of the Prior Art

The use of a solid inner stylet to guide the insertion and proper placement of a more flexible coaxial outer catheter is known. Examples of this art may be seen in U.S. Pat. No. 4,020,829, issued to Wilson et al. and U.S. Pat. No. 4,215,703, also issued to Wilson. These references teach the guiding of the flexible catheter using such a solid inner stylet wire. To accomplish the desired result, a solid inner stylet wire is given a permanent bend or other shape which causes the catheter to be so bent upon insertion of the inner stylet.

Also common is the use of a stylet for straightening a catheter-like device, which itself has been permanently impressed with a bend or other desired shape. This is particularly prominent in pacing leads or other electrode applications. Examples of electrodes having a predetermined shape may be found in U.S. Pat. No. 3,890,977, issued to Wilson and U.S. Pat. No. 4,136,703, issued to Wittkampf. These references teach the building of an implantable lead with particular reference to a "J" shape for insertion within the atrium of a human heart. The electrodes taught by Wilson and Wittkampf apparently use only the resiliency of the lead itself to maintain contact between the electrode and the stimulatable tissue. Insertion of these "J"-shaped leads is greatly facilitated through the use of a solid inner stylet which, in this case, tends to have a straightened shape for straightening the bend normally fixed within the distal end of the lead.

Leads having positive fixation means are also known in the art. Endocardial leads having a helical fixation means are taught in U.S. Pat. Nos. 4,146,036 4,209,019 and 4,217,913 all issued to Dutcher, et al. Each of these references teaches a body implantable lead for transvenous implantation primarily oriented to implantation within the right ventricle. A stiffening stylet is used to aid in implantation. Torque applied to the stylet is used for fixedly attaching the helical fixation means. In each case, however, the lead must be disposed in a nearly straight fashion and the stiffening stylet used must be nearly straight to enable proper imposition of torque by twisting motion of the stylet.

It has been shown to be desirable to implant a lead such as taught in the Dutcher references discussed above within the right atrium. The most desirable implantation attitude would involve fixation of the helical fixation means in the right atrial appendage. A "J" shape could be imparted to the implantable lead by using a shaped stylet as taught by Willson, et al. in the references discussed above, or by shaping the lead itself as taught in the references by Wilson and Wittkampf. Shaping the stylet would tend to cause difficulty in transmitting torque from the proximal and distal ends of the stylet to enable attachment of the fixation means. In fact, if one would take the stylet taught in the Dutcher references above and impart a "J" shape to it, it would become no longer useful for attaching the helical fixation means.

Shaping the body implantable lead using memory coils or other techniques as taught by Wilson and Wittkampf would allow the stylet to impart the necessary torque. However, this technique is disadvantageous because it makes fabrication of the lead relatively more expensive and increases the handling difficulty because the stylet is normally much stiffer than the body of the implantable lead. This means that the stylet, after being inserted for the purposes of attaching the helical fixation means, would tend to remove the "J" shape from the body of the implantable lead.

SUMMARY OF THE INVENTION

The present invention overcomes these difficulties through the use of a two-piece stylet. The two-piece stylet is inserted within a body implantable lead such as is taught the Dutcher references. A first, inner portion of the stylet is a solid stiffening wire. This inner portion is shaped by the implant physician in the desired manner, to provide for easy implantation. For most atrial applications, this shape will be a "J" or modified "J". The "J" shape will allow for attachment at the desired position within the atrial appendage. Depending upon the exact implantation technique used, a second solid stylet wire may be used first to locate the distal end of the implantable lead within the atrium. This would ease the transvenous insertion process. The shaped stylet would then be inserted to insure that the distal end of the implantable lead assumes a "J" shape.

The second portion of the stylet is a helically wound coil which is fitted coaxially outside of the first solid portion. Because of its coil shape, the second portion of the stylet is much more flexible and therefore, does not determine the shape of the distal end of the implantable lead as does the first portion. The function of the second portion of the stylet is to enable the transmission of a torque applied by the implant physician at the proximal end to be transmitted to the helical fixation means located on the distal end of the lead. The transmission of this torque allows the helical fixation means to be screwed into the endocardial tissue. Notice that, because of this flexibility, the second portion of the stylet will allow this torque to be transmitted notwithstanding the shape chosen for the inner solid portion.

The combined two-piece stylet taught herein is inserted within the central lumen of the body implantable lead in the normal fashion. Notice also that the second portion of the stylet may be shaped instead to impart a desired curvature to the distal end of the lead. This can be accomplished using memory coil technology. It is necessary however, that the torque transmitting portion of the stylet be substantially more flexible than the shaping portion.

BRIEF DESCRIPTION OF THE DRAWINGS

FIG. 2 is a plan view of the first inner portion of the improved stylet.

FIG. 3 is a plan view of the second outer portion of the stylet.

FIG. 4 is an end view of the proximal end of the second outer portion of the stylet.

FIG. 5 is an end view showing the distal end of the second outer portion of the stylet.

FIG. 6 is a cross-sectional view of the assembled stylet.

DETAILED DESCRIPTION OF THE PREFERRED EMBODIMENTS

Whereas the present description concentrates primarily upon a body implantable lead having a two-piece stylet wherein the first inner portion is one which imparts the desired shape to the implantable lead, and the second outer portion of the stylet is used for the transmission of torque from the proximal to the distal end, those of ordinary skill in the art will readily appreciate that the functions of the inner and outer portions of the stylet may be reversed. To do so, is well within realm of present technology although it would appear that this would render an embodiment of the present invention which is less desirable because it would be more costly.

Figure 1:
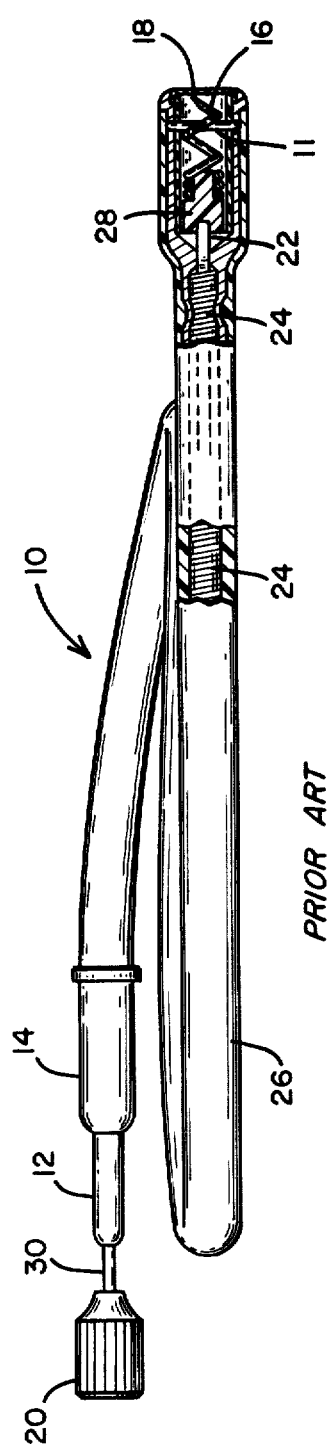
FIG. 1 shows a prior art endocardial lead having helical fixation means using a prior art stylet.

FIG. 1 is a plan view of a body implantable lead with stiffening stylet inserted. This body implantable lead is known in the prior art as taught by Dutcher, et al in U.S. Pat. No. 4,217,913 which is incorporated herein by reference. As explained therein, body implantable lead 10 has a proximal end with electrical connector 14 and terminal pin 12 which is connected via conductor coil 24 to the ring electrode and separate, electrically isolated fixation means 16 located at the distal end. The main body of the lead is covered with outer sheath 26 as shown. Stiffening stylet 30 is a solid piece of wire such as stainless steel, which is connected to torque receiving body 28 at position 22. As the implant physician turns knob 20, this torque is transmitted via stylet wire 30 to helical fixation means 16 which is screwed past fixed member 11 causing sharpened tip 18 to become fixedly engaged within the endocardial tissue.

FIG. 2 shows the solid inner portion of an improved stylet. Again, stylet knob 20 is attached at the proximal end of stylet wire 30. Different from the prior art, however, distal end 34 is foreshortened such that, if implanted within the body implantable lead (see also FIG. 1), distal tip 34 would not reach torque receiving body 28. In addition to being foreshortened, solid stylet wire 30 is also shaped to contain a bend at reference 32. This bend is preferably "J" shaped for insertion of the body implantable lead into the atrium. However, other shapes may be found desirable for other applications.

FIG. 3 shows the second outer portion of the improved stylet. The main body of the second portion of the stylet is a flexible, torque transmitting member (e.g., tube, coil, etc.). Coil 40, used in the preferred embodiment, is arranged helically and has an inner lumen for the insertion of stylet wire 30 (see also FIG. 2). Coil 40 may be of a variety of materials. It has been found that stainless steel and body compatible organic plastics have both proven satisfactory.

The proximal end of coil 40 is attached to stylet housing 36. This is enlarged to create knob 38, having knurled portions 46 as shown. As is common in the manufacture of stylets, the proximal portion 36 and knob 38 may be constructed of conveniently compatible plastic material. The distal end of coil 40 contains torque transmission tool 44. This is shaped for proper insertion into torque receiving body 28 at position 22 (see also FIG. 1). Torque transmission tool 44 is welded or attached in another suitable manner at position 42 as shown.

FIG. 4 is an end view of the proximal end of knob 38. Lumen 50 is sufficiently large for the insertion of solid stylet wire 30 (see also FIG. 2). Funnel-shaped depression 48 surrounds lumen 50 to greatly facilitate insertion of distal tip 34 of solid stylet wire 30.

FIG. 5 is an end view of the distal end of the second portion of the improved stylet. As can be seen, torque transmission tool 44 has a rectangular cross section for transmitting torque to torque receiving body 28. Torque transmission tool 44 is attached at position 42 as mentioned above by welding or other suitable attachment means.

FIG. 6 is a cross-sectional view of the two-piece stylet as assembled. Notice that distal tip 34 of solid stylet wire 30 is foreshortened. Notice also that torque induced by the implanting physician by turning knob 38 is transmitted via coil 40 to torque transmission tool 44, without regard to the shape of solid stylet wire 30.

Figure 7:
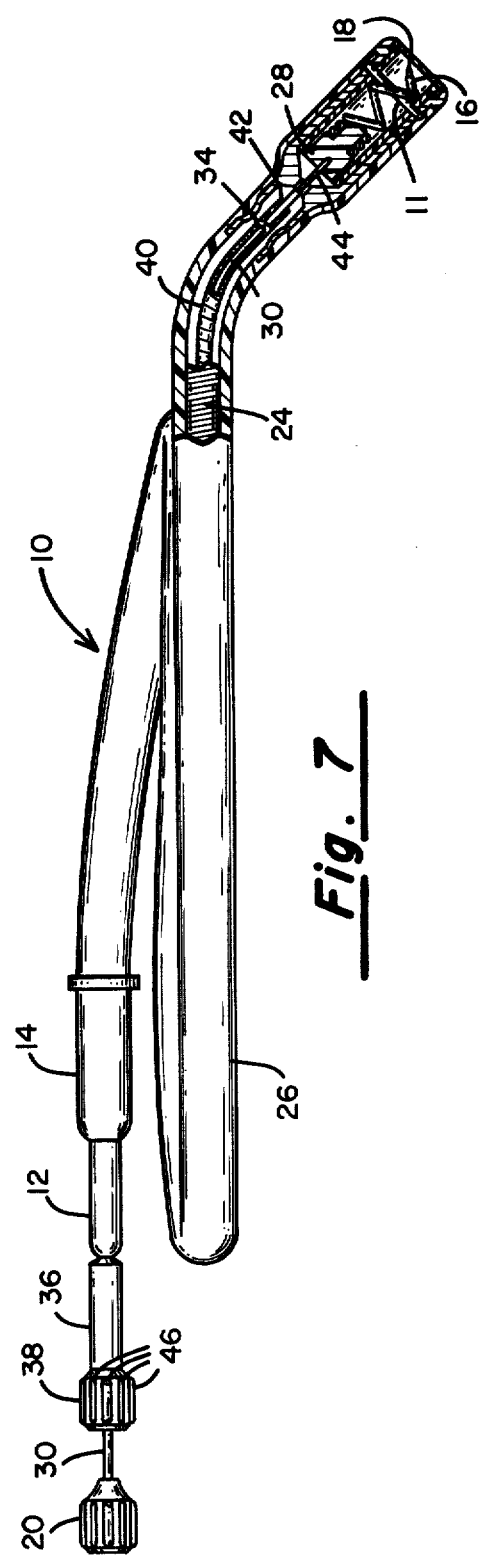
FIG. 7 is an assembled view of the body implantable lead with the two-piece stylet inserted.

FIG. 7 shows the entire assembled lead with the two-piece stylet in place. Notice that coil 40 fits coaxially within conductor coil 24 and solid stylet wire 30 fits coaxially within the lumen of coil 40. In its normal position, as explained above, solid stylet wire 30 is foreshortened such that distal tip 34 does not reach the very distal tip of the lead. Torque transmitting tool 44 is inserted in torque receiving body 28 at position 22 as explained in the Dutcher reference. During implantation the solid stylet wire 30 is used to impart shape to the main body of the lead. Torque applied to knob 20 permits the physician to control the implantation process. When the lead is properly affixed, knob 38 is turned, advancing helical fixation device 16 and causing pointed tip 18 to become securely lodged within the endocardial tissue.

Having thus described the preferred mode of practising the present invention those of ordinary skill in the art will be readily able to apply this present invention to other similar applications.

What is claimed is:

1. A body implantable lead comprising:
   a conductor having a proximal end and a distal end and having a lumen extending from said proximal end to said distal end;
   an insulating sheath covering said conductor;
   fixation means for securing said distal end of said conductor to body tissue; electrical connector attached to said proximal end of said conductor for electrically coupling said conductor to an electrical generator;
   stylet means removably located within said lumen of said conductor for imparting a curve to a portion of the distal end of the conductor for guiding placement of said distal end of said conductor; and
   flexible means, having a proximal end, rotatably and removably located within said lumen of said conductor coaxial to said stylet means for transferring torque induced at said proximal end of said flexible means to said fixation means while said stylet means imparts a curve to the distal end portion of said conductor.

2. A body implantable lead according to claim 1 wherein said stylet means is inserted coaxially within said flexible means.

3. A body implantable lead according to claim 2 wherein said fixation means is a helically wound fixation coil having a sharpened tip whereby said fixation means may be screwed into said body tissue.

4. A body implantable lead according to claim 1 or 2 or 3 wherein said stylet means is a solid stylet wire having a proximal end.

5. A body implantable lead according to claim 4 wherein said flexible means has a proximal end and a distal end and has a lumen extending from said proximal end to said distal end.

6. A body implantable lead according to claim 5 wherein said flexible means further comprises a knob fixedly attached to said proximal end of said flexible means.

7. A body implantable lead according to claim 6 wherein said flexible means is of a coil of body compatible metal.

8. A body implantable lead according to claim 6 wherein said flexible means is of a body compatible plastic.

9. A body implantable lead according to claim 7 wherein said stylet means further comprises a knob fixedly attached to said proximal end of said stylet wire.

10. A body implantable lead according to claim 8 wherein said stylet means further comprises a knob fixedly attached to said proximal end of said stylet wire.

11. A body implantable lead comprising:
a conductor having a proximal end and a distal end and having a lumen extending from said proximal end to said distal end;
an insulative sheath covering said conductor;
an electrode coupled to the distal end of said conductor;
electrical connector means attached to said proximal end of said conductor for electrically coupling said conductor to an electrical generator;
stylet means removably located within said lumen of said conductor for imparting a curve to a portion of the distal end of the conductor to guide the electrode to a desired position in the heart; and
flexible means, having a proximal end, rotatably and removably located within the lumen of said conductor coaxial to said stylet means for transferring torque induced at said proximal end of said flexible means to the distal end of said conductor while said stylet means imparts a curve to the distal end portion of said conductor.

12. A body implantable lead according to claim 11 wherein said stylet means is inserted coaxially within said flexible means.

13. A body implantable lead according to claim 11 or 12 wherein said stylet means is a solid stylet wire having a proximal end.

14. A body implantable lead according to claim 13 wherein said flexible means has a proximal end and a distal end and has a lumen extending from said proximal end to said distal end.

15. A body implantable lead according to claim 14 wherein said flexible means further comprises a knob fixedly attached to said proximal end of said flexible means.

16. A body implantable lead according to claim 15 wherein said flexible means is of a coil of body compatible metal.

17. A body implantable lead according to claim 15 wherein said flexible means is of a body compatible plastic.

18. A body implantable lead according to claim 16 wherein said stylet means further comprises a knob fixedly attached to said proximal end of said stylet wire.

19. A body implantable lead according to claim 17 wherein said stylet means further comprises a knob fixedly attached to said proximal end of said stylet wire.

* * * * *